US009138376B2

United States Patent
Allen

(10) Patent No.: US 9,138,376 B2
(45) Date of Patent: Sep. 22, 2015

(54) INTRAORAL ACUPRESSURE APPARATUS

(71) Applicant: INTRA ORAL TECHNOLOGIES, INC., Bend, OR (US)

(72) Inventor: James Peter Allen, Bend, OR (US)

( * ) Notice: Subject to any disclaimer, the term of this patent is extended or adjusted under 35 U.S.C. 154(b) by 2 days.

(21) Appl. No.: 14/618,846

(22) Filed: Feb. 10, 2015

(65) Prior Publication Data

US 2015/0164740 A1    Jun. 18, 2015

Related U.S. Application Data

(60) Continuation of application No. 14/456,183, filed on Aug. 11, 2014, which is a division of application No. 13/415,734, filed on Mar. 8, 2012, now abandoned, which is a continuation-in-part of application No. 12/592,297, filed on Nov. 23, 2009, now abandoned.

(51) Int. Cl.
*A61B 17/00* (2006.01)
*A61H 39/04* (2006.01)
*A61C 9/00* (2006.01)

(52) U.S. Cl.
CPC .............. *A61H 39/04* (2013.01); *A61C 9/0006* (2013.01)

(58) Field of Classification Search
CPC ........ A61H 39/04; A61C 9/0006; A61C 7/08; A61C 5/007; A61F 5/56
USPC ........... 433/2, 6–7, 25, 34, 71, 249, 264, 425, 433/37–38, 168.1, 213–215, 29, 199.1, 433/200.1; 128/861–862, 848; 606/204
See application file for complete search history.

(56) References Cited

U.S. PATENT DOCUMENTS

| 3,827,146 | A |   | 8/1974 | Wallshein |   |
|---|---|---|---|---|---|
| 3,923,064 | A |   | 12/1975 | Leupold |   |
| 3,994,068 | A |   | 11/1976 | Goshgarian |   |
| 4,073,296 | A |   | 2/1978 | McCall |   |
| 4,299,568 | A |   | 11/1981 | Crowley |   |
| 4,319,574 | A |   | 3/1982 | Sun et al. |   |
| 4,738,259 | A | * | 4/1988 | Brown et al. | 128/859 |
| 4,979,516 | A | * | 12/1990 | Abraham, II | 600/590 |
| 4,983,122 | A | * | 1/1991 | Mitnick | 433/229 |
| 5,250,067 | A |   | 10/1993 | Gelfer et al. |   |
| 5,284,161 | A | * | 2/1994 | Karell | 128/848 |
| 5,709,647 | A |   | 1/1998 | Ferber |   |
| 5,735,143 | A |   | 4/1998 | Tanaka |   |
| 5,792,067 | A | * | 8/1998 | Karell | 600/534 |

(Continued)

OTHER PUBLICATIONS

Allan Kalamir et al., Intra-Oral Myofascial Therapy for Chronic Myogenous Temporomandiublar Disorders: a Randomized, Controlled Pilot Study, 2010, 8 pages.

(Continued)

*Primary Examiner* — Amy R Weisberg
(74) *Attorney, Agent, or Firm* — Leber Patent Law P.C.

(57) ABSTRACT

An intraoral acupressure apparatus and method of treating a user are disclosed. The apparatus may include a base shaped to conform to a palate of a user, the base configured to be removably held adjacent to the palate in a predetermined position relative to acupressure points located on the user's palate. The apparatus may additionally include one or more projections extending out from the base and configured to contact one or more acupressure points of the user's palate when the apparatus is removably held in the predetermined position. The base may be configured to be removably held in the predetermined position without wire hooks or clasps.

10 Claims, 3 Drawing Sheets

(56) References Cited

U.S. PATENT DOCUMENTS

| | | | |
|---|---|---|---|
| 5,792,176 | A | 8/1998 | Chang |
| 6,261,306 | B1 | 7/2001 | Kramer |
| 6,299,586 | B1 | 10/2001 | Cao |
| 6,446,631 | B1* | 9/2002 | Hagiwara ............ 128/848 |
| 6,505,627 | B2* | 1/2003 | Kittelsen et al. ........ 128/859 |
| 6,510,853 | B1* | 1/2003 | Kittelsen et al. ........ 128/859 |
| 6,676,616 | B1* | 1/2004 | Hagiwara ............ 601/139 |
| 6,766,802 | B1* | 7/2004 | Keropian ............ 128/848 |
| 6,954,668 | B1 | 10/2005 | Cuozzo |
| 7,451,767 | B2 | 11/2008 | Keropian |
| 7,610,919 | B2* | 11/2009 | Utley et al. ............ 131/270 |
| 2002/0144689 | A1* | 10/2002 | Kittelsen et al. ........ 128/861 |
| 2003/0059737 | A1* | 3/2003 | Hall ................ 433/25 |
| 2006/0289013 | A1* | 12/2006 | Keropian ............ 128/848 |
| 2008/0210244 | A1* | 9/2008 | Keropian ............ 128/848 |
| 2009/0078275 | A1* | 3/2009 | Hegde et al. ........ 128/848 |
| 2009/0173352 | A1* | 7/2009 | Bhat et al. ............ 128/848 |
| 2011/0171592 | A1 | 7/2011 | Wittbold |
| 2012/0037168 | A1 | 2/2012 | Jackson |
| 2012/0109051 | A1 | 5/2012 | Harrell |
| 2013/0298916 | A1* | 11/2013 | Alvarez et al. ........ 128/861 |
| 2014/0190491 | A1* | 7/2014 | Garcia ............ 128/861 |

OTHER PUBLICATIONS

Martina Schmid-Schwap et al., Oral Acupunture in the Therapy of Craniomandibular Dysfunction Syndrome—a Randomized Controlled Trial (RCT), 2006, 7 pages.

Amompong Vachiramon, DDS, DBA, Msc(OMS, MSc(Ortho) et al., The Use of Acupuncture in Implant Dentistry, Mar. 2004, 7 pages.

Burton H. Goldstein, DMD, MS, FRCD(C), Unconventional Dentistry: Part V. Professional Issues, Concerns and Uses, Dec. 2000, 3 pages.

Steven K.H. Aung, M.D. FAAFP, Traditional Chinese Medicine in Modern Dentistry, Dec. 1998, 5 pages.

US office action, U.S. Appl. No. 12/592,297, Dec. 8, 2011, 18 pages.

Stewart's Clinical Removable Partial Prosthodontics, Phoenix et al., 2003, pp. 475-491.

\* cited by examiner

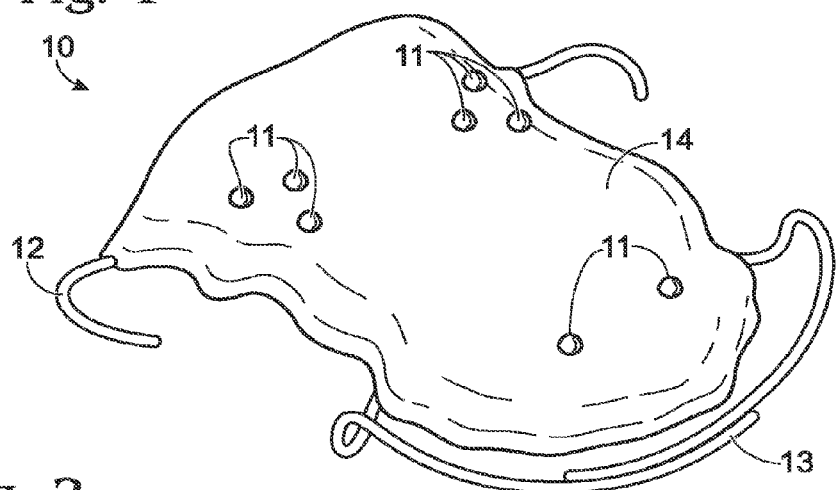
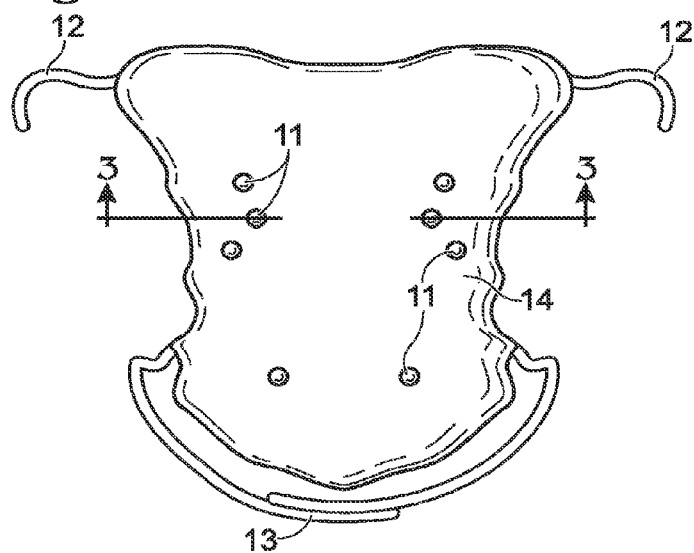
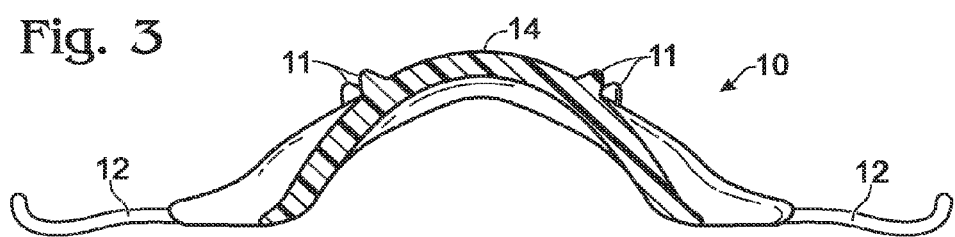

INTRAORAL ACUPRESSURE APPARATUS

CROSS-REFERENCE TO RELATED APPLICATIONS

This application is a continuation of U.S. patent application Ser. No. 14/456,183, filed Aug. 11, 2014, which is a divisional of U.S. patent application Ser. No. 13/415,734, filed Mar. 8, 2012, now abandoned, which is a continuation-in-part of U.S. patent application Ser. No. 12/592,297, filed Nov. 23, 2009, now abandoned, which are incorporated by reference in their entirety for all purposes.

BACKGROUND OF THE DISCLOSURE

The present disclosure relates to acupressure treatment and more specifically to a method and apparatus for applying pressure and/or stimulation to intraoral sites to elicit a response in a person. For example, the apparatus may be used to elicit responses for habit control, smoking, weight loss, anxiety treatment and/or other responses from acupressure/acupuncture stimulation.

Examples of related devices include U.S. Pat. No. 4,073,296 issued to McCall, which discloses an acupressure device for the ear. Other acupressure devices for the ear includes U.S. Pat. No. 5,735,143 issued to Tanaka and U.S. Pat. No. 4,319,574 issued to Sun. Other patents describe devices that are used on the human hand and provide a means of applying the stimulus to various parts of the body, including U.S. Pat. No. 3,923,064 issued to Leupold and U.S. Pat. No. 6,299,586 issued to Cao. Finally, other patents described devices that may be applied to the skin of various areas on the body, including U.S. Pat. No. 5,709,647 issued to Ferber, U.S. Pat. No. 5,792,176 issued to Chang, and U.S. Pat. No. 5,250,067 issued to Gelfer et al. The complete disclosures of the above patents are hereby incorporated by reference for all purposes.

SUMMARY OF THE DISCLOSURE

The present disclosure includes an apparatus made to cover the palatal area or the upper mouth. The apparatus may be either a complete or partial covering of the palate. This appliance has projections that extend towards the palate into and onto the tissues to stimulate areas of acupressure/acupuncture stimulation. These projections may be fixed or adjustable. The adjustments to the projections would be to modify the depth, extension, and/or place of acupressure/acupuncture stimulation.

It has been shown that applying stimulation through a manner of acupressure/acupuncture to sites intraorally by using an intraoral appliance may elicit a response used in habit control, such as elicit physiological responses for smoking, weight loss, anxiety treatment and/or other responses from acupressure/acupuncture stimulation.

The appliance may be held or retained by wires, clasps, suction, adhesives, cohesion and/or precision of fit. The fabrication of the appliance may be through direct methods in the mouth and/or indirect methods. The indirect methods may include impressions, models, 3-D scans, radiology modeling, ultra-sound, and/or other techniques to render models and forms of the palate and other areas of the mouth. The models may be castings, plaster, and/or digital models to be used in fabrication of the appliances.

The appliances may be fabricated using resins, polymers, metals, plastics, and/or other rigid and/or flexible material(s) and/or combinations of materials. The projections from the palatal side of the appliance may vary in location, depth, and/or shape. The location may vary with patient anatomy and required area of acupressure/acupuncture stimulation.

BRIEF DESCRIPTION OF THE DRAWINGS

FIG. 1 is a side perspective view of an example of an intraoral acupressure apparatus.

FIG. 2 is a top plan view of the intraoral acupressure apparatus of FIG. 1 with the projections located at spots corresponding to acupressure treatment areas.

FIG. 3 is a sectional view of the intraoral acupressure apparatus of FIG. 1 taken along lines 3-3 in FIG. 2.

DETAILED DESCRIPTION OF THE DISCLOSURE

FIG. 1 is a perspective view of an intraoral acupressure apparatus 10 that may be formed to a particular user's palate. Unless explicitly stated, intraoral acupressure apparatus 10 may additionally, or alternatively, include one or more components of one or more other intraoral acupressure apparatus described in the present disclosure. The palate apparatus 14 is initially made from an impression of the user's palate. The impression is typically made from one of many suitable materials used in surgical and/or dental applications and may be made from any acceptable method for making a direct or indirect impression of the palate region of the mouth.

Once the impression of the user's palate has been made, an apparatus of the impression is created using one or more suitable materials, such as plastics, polymers, resin, and/or a combination of materials to create a thin rigid yet somewhat flexible cast of the user's palate. After the apparatus has been made, acupressure points are located on the apparatus that will correspond to areas on the palate that are known to have areas that may be stimulated for acupressure treatment. These acupressure points will vary depending on the anatomy of the user. In one example, the acupressure points on the palate are located and marked with a surgical marking pen on the user's palate. The markings are transferred to the impression and then located on the palate apparatus 14. The projections 11 are then located on the palate apparatus 14. The areas of acupressure are indicated intra orally and this information transferred to the final model.

Once the acupressure points have been located on the apparatus of the palate, projections 11 are added to the apparatus that extend out the top of the palate apparatus. The projections may have various shapes including bead, spherical, nodule, spike and/or pointed. The size of the projection may vary and may be adjusted. When the palate apparatus is worn by the user, the projections 11 extend into the soft tissue of the user's palate stimulating that region of the user's palate.

The palate apparatus 14 apparatus may be kept in place using various means. In the figures, the palate apparatus is kept in place by adding wire hooks 12 and 13 to the palate apparatus that secures the apparatus to the user's palate. Other means for keeping the palate apparatus in place in the user's mouth are available, including clasps, suction, adhesives, cohesion, and/or precision fit.

Figure 4:
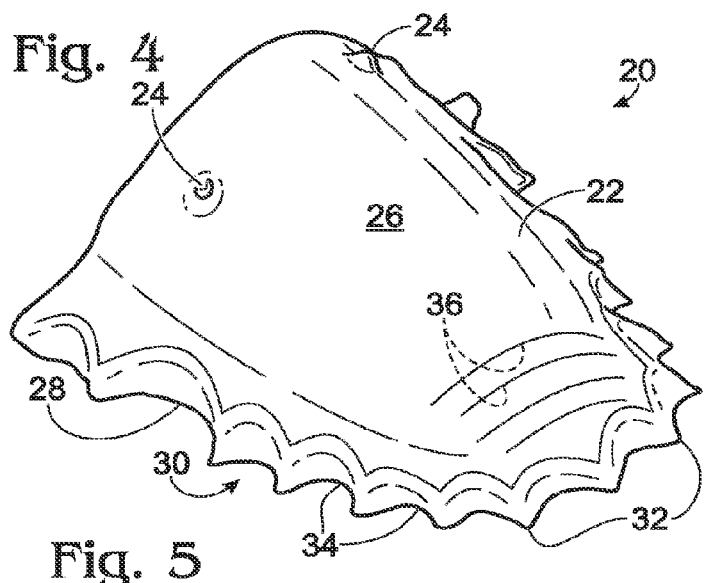
FIG. 4 is a side perspective view of another example of the intraoral acupressure apparatus of FIG. 1.
Figure 5:
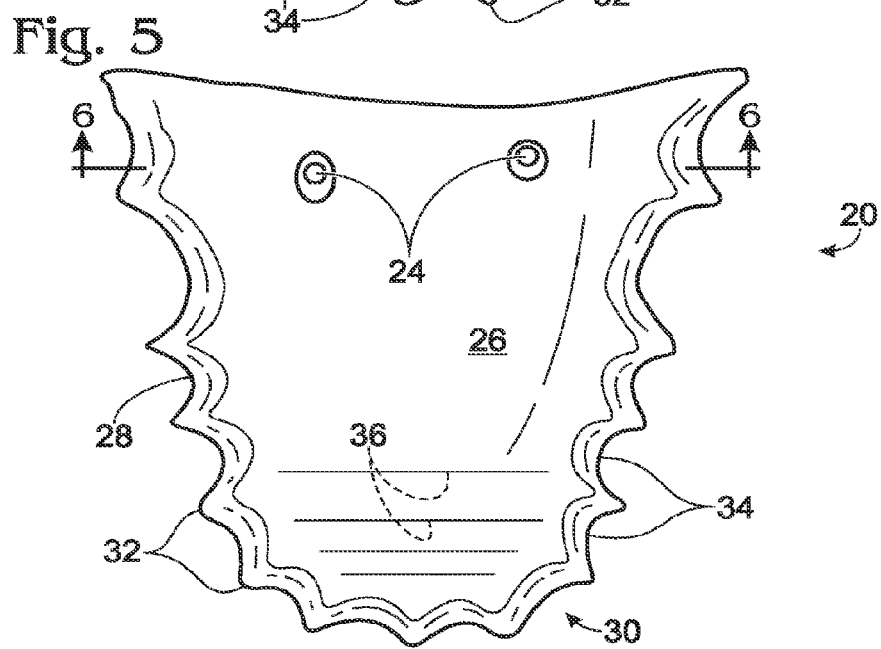
FIG. 5 is a top plan view of the intraoral acupressure apparatus of FIG. 4.
Figure 6:
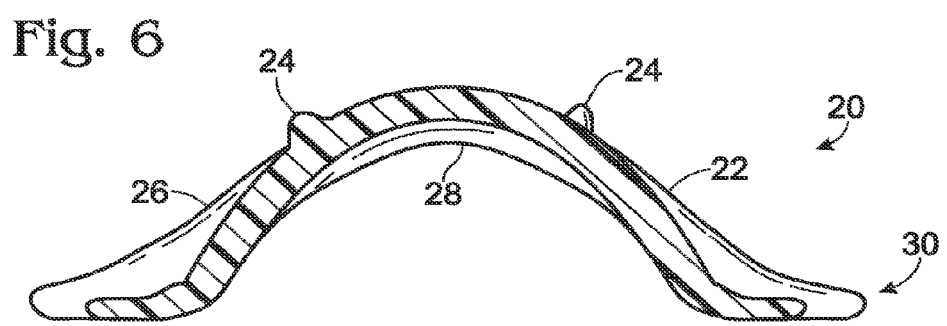
FIG. 6 is a sectional view of the intraoral acupressure apparatus of FIG. 4 taken along lines 6-6 in FIG. 5.

FIGS. 4-6 show another example of intraoral acupressure apparatus 10, which is generally indicated at 20. Unless explicitly stated, intraoral acupressure apparatus 20 may additionally, or alternatively, include one or more components of one or more other intraoral acupressure apparatus described in the present disclosure. Intraoral acupressure apparatus 20 may include any suitable structure configured to provide acupressure stimulation to the palate of the use. Apparatus 20 may be manufactured and/or made in any suitable way(s). For example, apparatus 20 may be custom made to a user's palate.

The intraoral acupressure apparatus may, for example, include a base 22 and one or more projections 24. The base may include a palate surface 26 and a lingual surface 28. The base may be configured to be inserted into a user's mouth placed adjacent to the palate in a predetermined position. When in the predetermined position, the palate surface may be adjacent to the palate and the lingual surface may be spaced from the palate relative to the palate surface (and/or adjacent to a user's tongue relative to the palate surface). In other words, the palate surface may face the user's palate, while the lingual surface may face away from the palate in the predetermined position.

In some examples, base 22 may be free from or without any apertures or openings. In some examples, base 22 may be configured to not restrict movement of the user's tongue. Specifically, base 22 may be configured to be free from and/or without structure(s) that hold a user's tongue down (such as to ensure the tongue does not obstruct a person's airway).

The base may be shaped to conform to a palate of a user. For example, the base may be arcuate in shape (as shown in FIGS. 4 and 6) to correspond to the arcuate shape of a user's palate. In some examples, the base may cover a substantial portion or all of the user's palate. Base 22 may be made from one or more polymer materials and/or other materials discussed in the present disclosure. In some examples, base 22 may be made with one or more materials configured to allow inspection of the user's palate when the base is removably held in the predetermined position. Such materials may, for example, allow inspection of the user's palate for one or more pressure points outside of the one or more acupressure points contacted by the projection(s) when the base is removably held in the predetermined position. Those pressure points may, in some examples, appear as blanched tissue.

Additionally, base 22 may be configured to be removably held adjacent to the palate in a predetermined position relative to acupressure points located on the user's palate. The predetermined position may, for example, include a position in which projections 24 contact and/or provide acupressure to one or more areas of the user's palate but in which the base does not apply pressure (or applies minimal pressure) to any other areas of the user's palate or mouth. Base 22 may be removably held in the predetermined position without wire hooks and/or clasps (such as wire hooks and/or clasps that attach the base to a user's teeth). For example, base 22 may be removably held in the predetermined position via a precision fit in the user's mouth.

Figure 8:
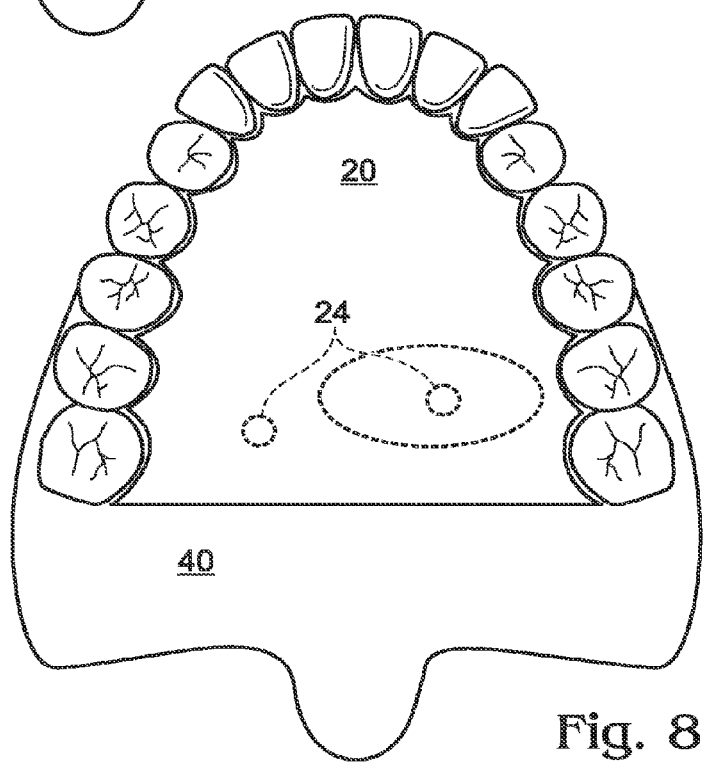
FIG. 8 is a schematic view of the user's palate of FIG. 7, shown with the intraoral acupressure apparatus of FIG. 4 installed.

An example of a precision fit may include where the base is configured not to contact any side of the user's teeth, other than the lingual sides of one or more of the user's teeth, when the base is removably held in the predetermined position. For example, the base may include a perimeter (or perimeter portion) 30 that includes a plurality of ridges 32 and a plurality of depressions 32 shaped to conform to the inner sides (and/or lingual sides) of one or more of the user's teeth. An example of apparatus 20 in the predetermined position is shown in FIG. 8.

In some examples, the lingual surface may have texture 36 that is configured to facilitate removal of apparatus 20 from the predetermined position and/or from the mouth of the user. For example, texture 36 may include a plurality of grooves, protuberances, and/or other structure(s) configured to facilitate gripping of apparatus 20. Although FIGS. 4-5 show parallel grooves, texture 36 may alternatively, or additionally, include non-parallel grooves and/or non-parallel structure(s).

Projections 24 may include any suitable structure configured to contact one or more acupressure points and/or areas of a user's palate when the base is in the predetermined position. The projections may be attached to and/or formed with base 22, and/or may extend out from the base. Projections 24 may be any suitable shape(s) and/or size(s). For example, projections 24 may be about 4 mm in diameter and/or other suitable diameter(s). Although two projections 24 are shown, apparatus 20 may include any suitable number of projections, such as one, three, four, five, six, seven, or more.

Figure 7:
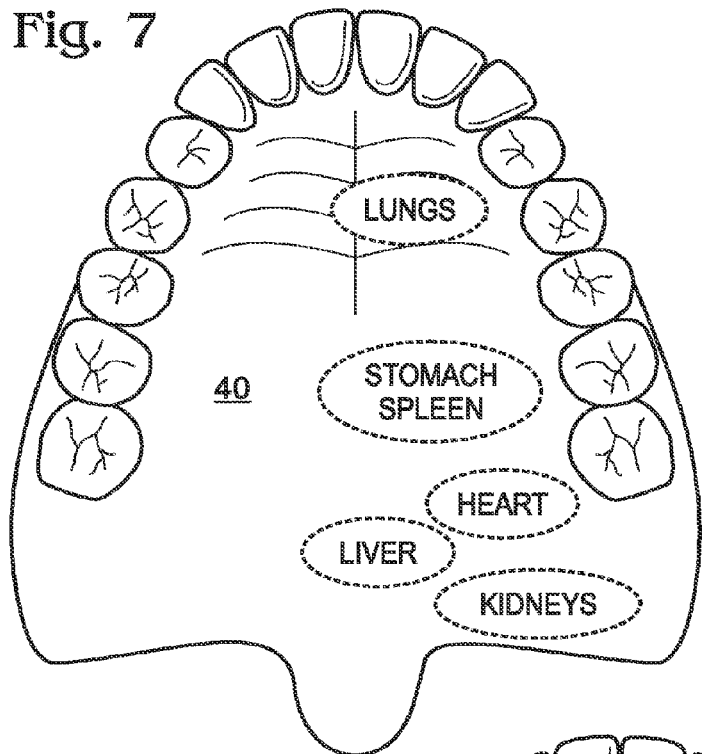
FIG. 7 is a schematic view of a user's palate and examples of areas of the user's palate that may affect other parts of the user's body.

In some examples, one or more of projections 24 may be configured to contact at least one acupressure point that promotes appetite suppression when the base is removably held in the predetermined position. Projections 24 may additionally, or alternatively, contact one or more other acupressure points that affect the same and/or other parts of a user's body. An example of acupressure points in a user's palate 40 is shown in FIG. 7, with apparatus 20 shown in the predetermined position in FIG. 8.

In some examples, the intraoral acupressure apparatus of the present disclosure may be described to have a "passive fit" when in the predetermined position in the user's mouth because it applies minimal pressure on a person's teeth and/or applies pressure only to the one or more acupressure points. "Minimal pressure," when used in the present disclosure to describe the passive fit of the apparatus in a person's mouth, refers to pressure that is less or substantially less than the pressure required to maintain and/or retain teeth in a position, such as a desired position following surgery and/or a desired position for realigning teeth. The intraoral acupressure apparatus may have a passive fit regardless on whether the apparatus is held or maintained in the predetermined position via wires, clasps, suction, adhesive, cohesion, and/or precision fit.

The intraoral acupressure apparatus of the present disclosure may be used in one or more methods of treating a user. Unless explicitly stated, the method of treating a user may include one or more steps described in making the apparatus above. Although particular steps are discussed, other examples of a method of treating a user may add, omit, replace, and/or modify one or more steps. In some examples, the method may include making an apparatus from an impression of a palate of a user, and placing a base of the apparatus in a predetermined position in the user's mouth. The apparatus may include a base configured to conform to the user's palate, the base configured to be removably held, without wire hooks or clasps, adjacent to the palate in a predetermined position relative to acupressure points located on the user's palate. The apparatus also may include one or more projections that extend out from the base and are configured to contact one or more acupressure points of the user's palate when the base is held in the predetermined position.

Making an apparatus from an impression of a user's palate may include forming an impression of the user's palate, creating a model of the base with the impression, placing acupressure points on the model (such as by making one or more depressions using a drill and/or other suitable device), pressing one or more materials (such as clear plastic) on the model, trimming excess material off, curing/hardening the material(s), removing the apparatus, and/or polishing the apparatus (if needed). Additionally, making an apparatus from an impression of a user's palate may include making the apparatus such that the base is configured to be removably held in the predetermined position via a precision fit in the user's mouth, such as being configured not to contact any side of the user's teeth other than the lingual sides of one or more of the user's teeth, when the apparatus is held in the predetermined position. For example, the apparatus may be made from an impression of a user's palate such that the base includes a perimeter portion having a plurality of depressions shaped to conform to the lingual sides of one or more of the user's teeth.

In some examples, the method of treating a user may further include inspecting the user's palate for one or more pressure points that are not the one or more acupressure points when the base is removably held in the predetermined position. This step may be facilitated if the base is made with one or more materials configured to allow inspection of the user's palate when the base is removably held in the predetermined position (covering most or all of the user's palate).

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the disclosure includes all novel and non-obvious combinations and subcombinations of the various elements, features, functions and/or properties disclosed herein.

Applicant reserves the right to submit claims directed to certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure. Where such claims recite "a" or "a first" element or the equivalent thereof, such claims should be understood to include incorporation of one or more such elements, neither requiring nor excluding two or more such elements.

What is claimed is:

1. A method of making a device for treating a user, the method comprising:

making an impression of a palate of a user,
   casting, from the impression, an accurate model of the palate;
   locating, on the model, one or more acupressure locations that correspond to areas on acupressure points on the palate of the user;
   removing material from the model to form a depression at each of the acupressure locations; and then
   forming, by casting a flowable material on the model, a device including
      a base configured to conform to the user's palate, the base configured to be removably held adjacent to the palate in a predetermined position relative to the acupressure locations, and
      one or more projections that extend from the base toward the palate at the acupressure locations to exert pressure on the acupressure locations when the base is held adjacent to the palate, the projections being formed by flow of the flowable material into the depressions during formation of the device.

2. The method of claim 1, further comprising configuring the base to be removably held in the predetermined position via a precision fit in the user's mouth.

3. The method of claim 2, further comprising configuring the base such that the base is configured not to contact any side of the user's teeth, other than lingual sides of one or more of the user's teeth to hold the device in the predetermined position when the device is in use.

4. The method of claim 3, further comprising configuring the base to include a perimeter portion having a plurality of depressions shaped to conform to the lingual sides of one or more of the user's teeth.

5. The method of claim 1 wherein the flowable material is selected to allow inspection of the user's palate when the device is in use.

6. The method of claim 1 wherein the projections are located to extend into soft tissue of the user's palate when the device is in use.

7. The method of claim 1 wherein the projections are in the form of beads or spheres.

8. The method of claim 1 wherein at least some of the projections are pointed.

9. The method of claim 8 wherein the projections are in the form of spikes.

10. The method of claim 1 wherein, when the device is in the predetermined position, the base applies minimal pressure or no pressure to all areas of the user's palate or mouth other than the acupressure locations.

* * * * *